United States Patent [19]

Paul

[11] Patent Number: 5,167,630

[45] Date of Patent: Dec. 1, 1992

[54] BLOOD VESSEL CANNULATION DEVICE

[76] Inventor: Kamaljit S. Paul, 3220 Old Orchard La., Oshkosh, Wis. 54901

[21] Appl. No.: 765,876

[22] Filed: Sep. 26, 1991

[51] Int. Cl.$^5$ ............................................. A61M 5/32
[52] U.S. Cl. ........................... 604/179; 128/DIG. 28; 604/174
[58] Field of Search ............... 604/179, 180, 174, 173, 604/175, 177, 176; 128/DIG. 26

[56] References Cited

U.S. PATENT DOCUMENTS

| | | | |
|---|---|---|---|
| 2,402,306 | 6/1946 | Turkel | 604/174 |
| 3,055,365 | 9/1962 | Tezak | 604/179 |
| 4,392,857 | 7/1983 | Beran | 604/179 |
| 4,569,675 | 2/1986 | Prosl et al. | 128/DIG. 26 |
| 4,585,443 | 4/1986 | Kaufman | 604/179 |
| 4,666,434 | 5/1987 | Kaufman | 604/179 |

*Primary Examiner*—Paul J. Hirsch
*Attorney, Agent, or Firm*—Depaoli & O'Brien

[57] ABSTRACT

This invention provides a cannulation device which is adapted for facilitating the location and venipuncture of a blood vessel with ease and precision. A carrier assembly supports a movable cubic block unit which contains an aligned combination of an ultrasonic probe and a cannula guide path means. The cubic block unit moves laterally within a defined space, whereby a blood vessel is located ultrasonically by by blood flow detection, and the guide path means assists venipuncture by a cannula.

9 Claims, 1 Drawing Sheet

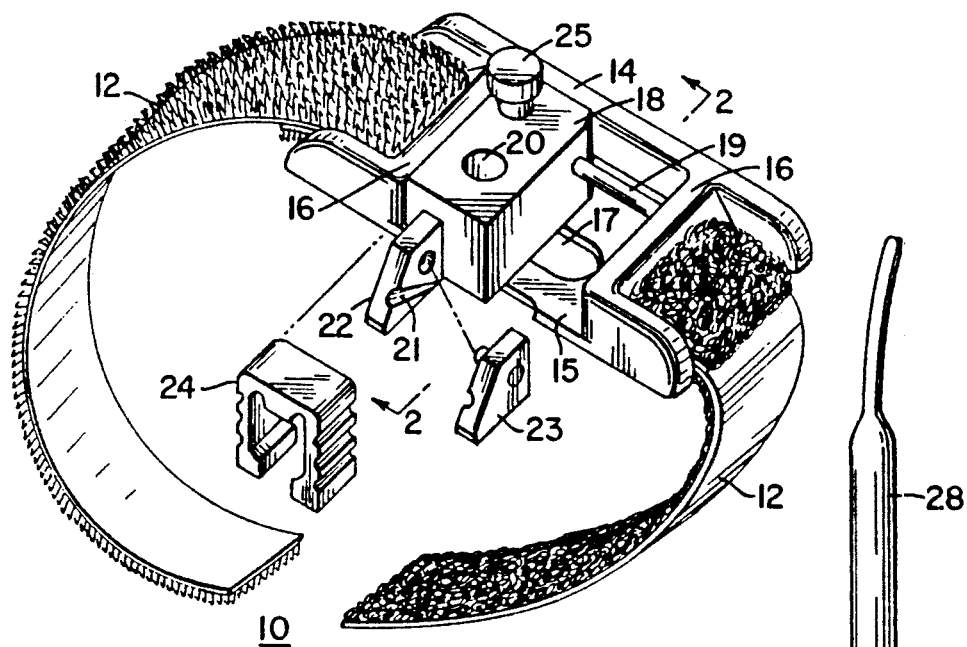
Fig.1
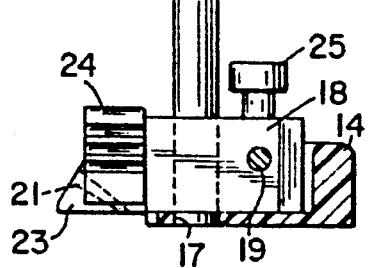
Fig.2
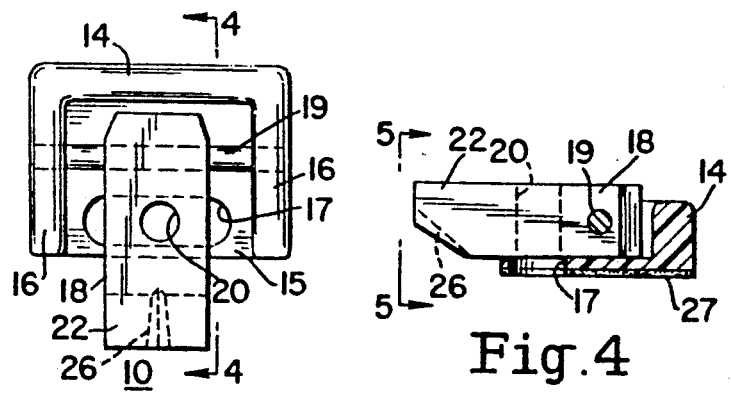
Fig.3
Fig.4
Fig.5

BLOOD VESSEL CANNULATION DEVICE

BACKGROUND OF THE INVENTION

A common procedure in medical practice is the insertion of a surgical cannula in a blood vessel of a patient for the purpose of monitoring blood pressure, obtaining blood samples, introducing medicinal dosages, or the like.

It is often difficult and tedious to locate and puncture a blood vessel of a patient who is in hypotension, or is obese and the blood vessel is not close to the skin surface, or the patient is elderly and the blood vessel is thickened and tends to displace during the cannulation procedure.

Various cannulation devices have been proposed for improving venipuncture procedures to ease inherent difficulties of the type noted above. Of particular interest with respect to the present invention are devices which utilize an ultrasonic probe and cannula guide means. Pertinent references include U.S. Pat. Nos. 4,029,084; 4,289,139; 4,387,721; and 4,667,679. Accurate guiding of a cannula relative to the blood vessel located by the ultrasonic probe is not easily accomplished with the type of cannulation devices described in the prior art.

There remains a need for new and improved devices to overcome the various difficulties associated with cannulation of blood vessels in patients.

Accordingly, it is an object of this invention to provide a cannulation device which has ultrasonic probe means and cannula guide means for locating and puncturing of blood vessels.

It is a further object of this invention to provide a cannulation device which locates a blood vessel ultrasonically and guides a puncturing cannula with ease and precision.

Other objects and advantages of the present invention shall become apparent from the accompanying description and drawings.

SUMMARY OF THE INVENTION

One or more objects of the present invention are accomplished by the provision of a blood vessel cannulation device comprising (1) a thin plate having an open slot section which extends between opposite sides of the plate; (2) a carriage unit which is slidably positioned on the plate surface for lateral movement over the open slot; (3) an annular tunnel down through the carriage unit which is normal to the plate and positioned over the open slot of the plate, and the annular tunnel is adapted for the insertion of a slender ultrasonic probe member with transmitting and receiving transducer elements, and supports a probe member within the carriage unit with the probe end in proximity with the open slot of the plate; and (4) a cannula guide path means at the front end of the carriage unit which is positioned in a longitudinally aligned acute angle with the tunnel axis in the carriage unit; wherein the device is adapted for secure placement on the skin surface of a patient in the vicinity of a blood vessel.

In a further embodiment this invention provides a blood vessel cannulation device comprising (1) a carrier assembly having a rectangular bottom plate and two raised edge members bordering opposite sides of the bottom plate which define a shallow interior space; (2) an open slot in the bottom which extends perpendicular to the two raised edge members; (3) a cubic block which is positioned within the assembly interior space and is slidably connected to the two raised edge members for lateral movement across the bottom plate; (4) an annular tunnel down through the cubic block which is normal to the bottom plate and positioned over the open slot of the bottom plate, and the annular tunnel is adapted for the insertion of a slender ultrasonic probe member with transmitting and receiving transducer elements, and supports a probe member within the cubic block with the probe end in proximity with the open slot of the bottom plate; and (5) a cannula guide path means at the front end of the cubic block, which is positioned in a longitudinally aligned acute angle with the tunnel axis in the cubic block; wherein the device is adapted for placement on the skin surface of a patient in the vicinity of a blood vessel, and in combination with an ultrasonic probe locates the blood vessel by lateral scan and pulsatile blood flow detection, and the guide path means is utilized to direct a venipuncture cannula at an acute angle into the localized blood vessel.

In a preferred embodiment this invention provides a blood vessel cannulation device comprising (1) a carrier assembly having a rectangular bottom plate and two raised edge members bordering opposite sides of the bottom plate which define a shallow interior space; (2) an open slot in the bottom plate which extends perpendicular to the two raised edge members; (3) a cubic block which is positioned within the assembly interior space and is slidably connected to the two raised edge members for lateral movement across the bottom plate; (4) an annular tunnel down through the cubic block which is normal to the bottom plate and positioned over the open slot of the bottom plate; (5) a slender ultrasonic probe member with transmitting and receiving transducer elements, which is supported within the annular tunnel of the cubic block with the probe end in proximity with the open slot of the bottom plate; and (6) a cannula guide path means at one end of the cubic block, which is positioned in a longitudinally aligned acute angle with the tunnel and ultrasonic probe axis in the cubic block; wherein the device is adapted for placement on the skin surface of a patient in the vicinity of a blood vessel, and the ultrasonic probe locates the blood vessel by lateral scan and pulsatile blood flow detection, and the guide path means is utilized to direct a venipuncture cannula at an acute angle into the localized blood vessel.

BRIEF DESCRIPTION OF THE DRAWINGS

FIG. 1 is a prospective view of a present invention blood vessel cannulation device with parts exploded for illustration.

FIG. 2 is a cross-section taken along lines 2—2 of FIG. 1.

FIG. 3 is a top plan view of a second blood vessel cannulation device embodiment.

FIG. 4 is a cross-section taken along lines 4—4 of FIG. 3.

FIG. 5 is a front elevation taken along lies 5—5 of FIG. 4.

DESCRIPTION OF INVENTION EMBODIMENTS

A present invention cannulation has dimensions which are practical for easy manipulation and placement on the skin surface of a patient, such as on the inner wrist area for purposes of locating and cannulating the radial artery of the wrist.

The shallow interior space defined by the two opposing raised edge members typically will be 20–25 mm×20–25 mm×8–12 mm in size.

The cubic block can have dimensions in the range of 10–15 mm×20–25 mm×8–15 mm. The annular tunnel down through the cubic block normally is circular in shape, and has dimensions sufficiently large for access by the ultrasonic probe member, e.g., a diameter between about 4–8 mm.

The cubic block is slidably connected to the two raised edge members for lateral movement. As illustrated in the drawings, the cubic block can slide along a rail connection by hand manipulation.

A present invention device preferably has a securing means for retaining the device on the skin surface of a patient, such as a Velcro type strap or a contact adhesive undercoating or the like.

The blood flow detector in a present invention device is an ultrasonic probe member which develops an output electrical signal which is responsive to pulsatile changes in blood flow through a blood vessel. A preferred blood flow detector is an ultrasonic probe with a Doppler effect, which is in combination with an external processing unit for converting detected backscattered ultrasound into an electrical signal having an audiofrequency amplifier means to reproduce an audible signal. Ultrasonic blood flow detection systems are commercially available from manufacturers such as Park Electronic Laboratories (Beaverton, Oreg.).

A present invention cannulation device can be fabricated with metal and/or plastic structural components. The device is designed for easy disassembly to facilitate cleaning and sterilizing. An invention device can be produced with inexpensive molded plastic components if a disposable version is contemplated. The plastic components can be injection molded from thermoplastic polymers such as polyethylene, polypropylene, polystyrene, polycarbonate, polyurethane, polyvinyl chloride, polyamide, polyester, and the like.

The present invention further contemplates the provision of an article of manufacture comprising a heat seal pouch which contains an invention cannulation device in a sterilized environment. The sealed pouch optionally can incorporate a color-coded sterilization indicator means, such as a chemically-treated paper strip.

In FIG. 1 a cannulation device 10 is illustrated which is constructed of molded plastic components, and has a Velcro strap securing means 12. Carrier assembly 14 has a rectangular bottom slate 15 and two raised edge members 16 which form a shallow interior space. Open slot 17 in bottom plate 15 extends between raised edge members 16.

Cubic block 18 is positioned in the interior space of assembly 14, and is slidably connected to raised edge members 16 on rail 19. Annular tunnel 20 passes downward through cubic block 18, and is positioned over open slot 17 in bottom plate 15.

Cannula guide path means 21 is positioned in front end 22 of cubic block 18, and is longitudinally aligned in an acute angle with the axis of tunnel 20 in cubic block 18. Front end 22 has removable section 23, and clip 24 retains section 23 in position during accessing of a cannula through guide path means 21. After a venipuncture procedure is completed, clip 24 and section 23 are disassembled, and device 10 is removed from the cannula which remains with its distal end in the punctured blood vessel. Spring bias means 25 retains cubic block 18 in position on rail 19 after manipulation.

In FIG. 3, cannula guide means 26 is an inverted V-shaped groove which angles downward in front end 22. The FIG. 3 device 10 can be removed from the guided cannula after venipuncture without any need for disassembly of front end 22. In FIG. 4, securing means 27 is a contact adhesive undercoating.

For purposes of venipuncture of the wrist radial artery of a patient, device 10 as shown in FIG. 1 and FIG. 2 is strapped to the patient's wrist with open slot 17 in a transverse position over the vicinity of the radial artery. Ultrasonic probe 28 is connected to an external processing unit for reproduction of an audible signal. Cubic block 18 with ultrasonic probe 28 in tunnel 20 is manipulated laterally until a peak intensity of the audible backscatter signal indicates the location of the radial artery. A cannula is urged through guide path means 21 to venipuncture depth in the radial artery. Front end 22 is disassembled and device 10 is removed from the patient's wrist.

A present invention cannulation device facilitates the accurate location of a blood vessel, and permits venipuncture with ease and precision in cases where such intervention usually is difficult.

What is claimed is:

1. A blood vessel cannulation device comprising (1) a thin plate having an open slot section which extends between opposite sides of the plate; (2) a carriage unit which is slidably positioned on the plate surface for lateral movement over the open slot; (3) an annular tunnel down through the carriage unit which is normal to the plate and positioned over the open slot of the plate, and the annular tunnel is adapted for the insertion of a slender ultrasonic probe member with transmitting and receiving transducer elements, and supports a probe member within the carriage unit with the probe end in proximity with the open slot of the plate; and (4) a cannula guide path means at the front end of the carriage unit, which is positioned in a longitudinally aligned acute angle with the tunnel axis in the carriage unit; wherein the device is adapted for secure placement on the skin surface of a patient in the vicinity of a blood vessel.

2. A blood vessel cannulation device comprising (1) a carrier assembly having a rectangular bottom plate and two raised edge members bordering opposite sides of the bottom plate which define a shallow interior space; (2) an open slot in the bottom plate which extends perpendicular to the two raised edge members; (3) a cubic block which is positioned within the assembly interior space and is slidably connected to the two raised edge members for lateral movement across the bottom plate; (4) an annular tunnel down through the cubic block which is normal to the bottom plate and positioned over the open slot of the bottom plate, and the annular tunnel is adapted for the insertion of a slender ultrasonic probe member with transmitting and receiving transducer elements, and supports a probe member within the cubic block with the probe end in proximity with the open slot of the bottom plate; and (5) a cannula guide path means at the front end of the cubic block, which is positioned in a longitudinally aligned acute angle with the tunnel axis in the cubic block; wherein the device is adapted for placement on the skin surface of a patient in the vicinity of a blood vessel, and in combination with an ultrasonic probe locates the blood vessel by lateral scan and pulsatile blood flow detection, and the guide path means is utilized to direct a venipuncture cannula at an acute angle into the localized blood vessel.

3. A blood vessel cannulation device comprising (1) a carrier assembly having a rectangular bottom plate and two raised edge members bordering opposite sides of the bottom plate which define a shallow interior space; (2) an open slot in the bottom plate which extends perpendicular to the two raised edge members; (3) a cubic block which is positioned within the assembly interior space and is slidably connected to the two raised edge members for lateral movement across the bottom plate; (4) an annular tunnel down through the cubic block which is normal to the bottom plate and positioned over the open slot of the bottom plate; (5) a slender ultrasonic probe member with transmitting and receiving transducer elements, which is supported within the annular tunnel of the cubic block with the probe end in proximity with the open slot of the bottom plate; and (6) a cannula guide path means at one end of the cubic block, which is positioned in a longitudinally aligned acute angle with the tunnel and ultrasonic probe axis in the cubic block; wherein the device is adapted for placement on the skin surface of a patient in the vicinity of a blood vessel, and the ultrasonic probe locates the blood vessel by lateral scan and pulsatile blood flow detection, and the guide path means is utilized to direct a venipuncture cannula at an acute angle into the localized blood vessel.

4. A device in accordance with claim 3 which has a securing means for retaining the device on the skin surface of a patient.

5. A device in accordance with claim 3 wherein the ultrasonic probe is a Doppler blood flow detector, and is in combination with an external processing unit for converting detected backscattered ultrasound into an electrical signal having an audiofrequency amplifier means to reproduce an audible signal.

6. A device in accordance with claim 3 wherein the cannula guide means is a V-shaped groove which angles downward from the front end to the bottom side of the cubic block.

7. A device in accordance with claim 3 wherein the cannula guide means is an acute angle passageway through a cubic block attachment which disassembles to release the cannula after blood vessel puncture.

8. An article of manufacture comprising a heat seal pouch which encloses a device of claim 1 under sterilized conditions.

9. An article in accordance with claim 8 which contains a color-coded sterilization indicator means.

* * * * *